(12) United States Patent
Ha et al.

(10) Patent No.: US 7,696,130 B2
(45) Date of Patent: *Apr. 13, 2010

(54) PNA CHIP USING PLASTIC SUBSTRATE COATED WITH EPOXY GROUP-CONTAINING POLYMER, METHOD OF MANUFACTURING THE PNA CHIP, AND METHOD OF DETECTING SINGLE NUCLEOTIDE POLYMORPHISM USING THE PNA CHIP

(75) Inventors: Jeongmin Ha, Changwon (KR); Jae Young Jang, Daejeon (KR); In Soo Kim, Daejeon (KR)

(73) Assignee: LG Life Sciences, Ltd., Seoul (KR)

( * ) Notice: Subject to any disclaimer, the term of this patent is extended or adjusted under 35 U.S.C. 154(b) by 707 days.

This patent is subject to a terminal disclaimer.

(21) Appl. No.: 11/156,653

(22) Filed: Jun. 21, 2005

(65) Prior Publication Data

US 2006/0147949 A1 Jul. 6, 2006

(30) Foreign Application Priority Data

Jun. 24, 2004 (KR) .................. 10-2004-0047677

(51) Int. Cl.
*C40B 50/18* (2006.01)
(52) U.S. Cl. .................. 506/32; 506/33; 435/7.1; 523/400
(58) Field of Classification Search .................. None
See application file for complete search history.

(56) References Cited

U.S. PATENT DOCUMENTS

| | | | | |
|---|---|---|---|---|
| 6,048,953 A | * | 4/2000 | Kawashima et al. | 526/318.4 |
| 2001/0031504 A1 | * | 10/2001 | Kim et al. | 438/1 |
| 2003/0109062 A1 | * | 6/2003 | Inomata et al. | 436/518 |

OTHER PUBLICATIONS

Hyrup et al (1996 Bioorganic & Medicinal Chemistry 4:5-23).*
1999 DNA Microarrays Editor: Mark Schena Oxford University Press, Oxford UK p. 101-120).*
Jaworek, et al. "*Radiation Curable Materials Principles and New Perspectives*"; Macromol Symp. 159, 197-204(2000).
Proudnikov, et al. "*Immobilization of DNA on Polyacrylamide Gel for the Manufacture of DNA and DNA-Oligonucleotide Microchips; Analytical Biochemistry*"; 259,34-41 (1998).
Nilsson, et al. "*Real Time Monitoring of DNA Manipulations Using Biosensor Technology*" ; Analytical Biochemistry 224,400-408 (1995).
Rogers, et al. "*Immobilization of Oligonucleotides onto a Glass Support via Disulfide Bonds: A Method for Preparation of DNA Microarrays*" Analytical Biochemistry ;266,23-30 (1999).
Rehman, et al. "*Immobilization of Acrylamide-Modified Oligonucleotides by Co-Polymerization*"; 1999 Ocford University Press.
Gerhold, et al. "*DNA Chips: Promising Toys Have Become Powerful Tools*"; TIBS May 24, 1999.
Higashi, et al. "Effects of Helical Sense and Macrodipole on Helix Interaction in Poly(glutamic acid) Monolayers at the Air-Water Interface"; Journal of Colloid and Interface Science 220, 362-366 (1999).
Nikiforov, et al. "The Use of 96-Well Polystyrene Plates for DNA Hybridization-Based Assays: An Evaluation of Different Approaches to Oligonucleotide Immobilization." Analytical Biochemistry 227, 201-209 (1995).

* cited by examiner

*Primary Examiner*—Christopher Low
*Assistant Examiner*—Christopher M. Gross
(74) *Attorney, Agent, or Firm*—McKenna Long & Aldridge LLP

(57) ABSTRACT

Provided is a PNA (Peptide Nucleic Acid) chip in which a probe PNA containing a desired DNA sequence is immobilized on a plastic substrate coated with an epoxy group-containing polymer. Therefore, single-stranded PNAs can be immobilized on a transparent plastic substrate by means of an epoxy group-containing polymer layer in an efficient and cost-effective manner. Fluorescence signal detection based on PNA/DNA hybridization enables identification of SNP (Single Nucleotide Polymorphism).

7 Claims, 11 Drawing Sheets

O Linker No. 3:

M Linker No. 4:

C6 Linker No. 5:

20% rtL 180m

20% rtL 180w

30% rtL 180m

30% rtL180w

PNA CHIP USING PLASTIC SUBSTRATE COATED WITH EPOXY GROUP-CONTAINING POLYMER, METHOD OF MANUFACTURING THE PNA CHIP, AND METHOD OF DETECTING SINGLE NUCLEOTIDE POLYMORPHISM USING THE PNA CHIP

CROSS-REFERENCE TO RELATED PATENT APPLICATION

This application claims priority from Korean Patent Application No. 10-2004-0047677, filed on Jun. 24, 2004, in the Korean Intellectual Property Office, the disclosure of which is incorporated herein in its entirety by reference.

FIELD OF THE INVENTION

The present invention relates to a PNA (Peptide Nucleic Acid) chip, and more particularly, to a PNA chip in which a probe PNA including a desired DNA sequence is immobilized on a plastic substrate coated with an epoxy group-containing polymer.

DESCRIPTION OF THE RELATED ART

Peptide Nucleic Acids (referred to as "PNAs", hereinafter) were originally developed as gene-targeting drugs. Due to good hybridization of PNAs with complementary DNAs, many reports about PNAs have been made. PNA/DNA hybridization is based on strong base pairing between PNA single strands and complementary DNA single strands. That is, the most prominent property of PNAs is excellent DNA recognition ability by stable hybridization with complementary DNAs. The structures of PNAs are very similar to those of DNAs. PNAs have a neutral peptide backbone unlike a negatively charged sugar-phosphate backbone of DNAs and N-(2-aminoethyl)glycine repeat units linked through an amide bond. It is known that four nucleobases contained in PNAs occupy similar spatial dimensions to four bases of DNAs and an intermolecular distance of PNAs is also almost the same as that of DNAs. Unlike DNAs, PNAs are not degraded by nuclease or protease, and thus are biologically very stable. Furthermore, while thermal stability of DNA duplexes is affected by salt concentration due to a negatively charged DNA backbone, thermal stability of PNA/DNA duplexes is fundamentally not affected by salt concentration due to the neutral backbone of PNAs. The low salt-concentration dependency of PNA/DNA duplexes reduces an electrostatic repulsion between PNAs and DNAs, thereby increasing the thermal stability of the PNA/DNA duplexes. Due to these many advantages of PNAs, PNAs have received great interest in biologically important or diagnostic applications that cannot be approached by traditional DNA-related methods.

PNA immobilization technology has been studied in a similar way to DNA immobilization technology. Most of currently available DNA immobilization methods are based on immobilization of single-stranded DNAs capable of hybridizing with analytes. A method of adsorbing DNAs onto a solid surface is mainly used (Nikiforov and Rogers, *Anal Biochem.* 1995). A hybridization method (Proudnikov et al., *Anal Biochem.* 1998; Rehman et al., *Nucleic Acids Res.* 1999) and a complex formation method (Nilsson et al., *Anal Biochem.* 1995) have been developed as well. Photolithography is widely known as a process of immobilizing oligonucleotides mainly chemically synthesized (Gerhold et al., *Trends Biochem Sci.* 1999). A covalent bond between a support and a reactive group incorporated into oligonucleotides is mediated by a silane monolayer (Rogers et al., *Anal Biochem.* 1999), a self-assembled monolayer (Higashi et al., *J Colloid Interface Sci.* 1999), etc. In the above methods, immobilization of biological substances by a physical method such as adsorption is spatially or structurally restricted and has a detection limit such as high background signal due to non-specific adsorption. Furthermore, since epoxy silane can be coated on a glass substrate but not on a plastic substrate, substrate modification is restricted.

The arrays of biomolecules or polymers may be manufactured by spotting, microarray technology, photolithography, or electronic addressing. The spotting is dropping of biomolecules on desired positions by three-dimensional movement of microrobots and the microarray technology is microarray formation using fountain pen-like pins. The photolithography modifies a surface by selectively illuminating light on desired positions to adhere biomolecules to only the desired positions of the surface and the electronic addressing is carried out by selective application of an electrode voltage to a microelectrode array to immobilize biomolecules only on a predetermined electrode. In the present invention, a PNA array is made by non-contacting inkjet printing spotting.

While searching for solutions to the above problems of the prior art, the present inventors found that incorporation or coating of an epoxy group-containing polymer on a universal plastic substrate enabled efficient and cost-effective immobilization of PNAs, and thus completed the present invention.

SUMMARY OF THE INVENTION

The present invention provides a novel PNA chip capable of immobilizing PNAs on a universal plastic substrate in an efficient and cost-effective manner.

The present invention also provides a method of efficiently manufacturing the PNA chip.

The present invention also provides a method of detecting SNP (Single Nucleotide Polymorphism) using the PNA chip.

According to an aspect of the present invention, there is provided a PNA chip in which a probe PNA containing a desired DNA sequence is immobilized on a plastic substrate coated with an epoxy group-containing polymer.

In the present invention, the plastic substrate may be any plastic substrate that can be coated with a polymer. Preferably, the plastic substrate is a transparent plastic substrate made of a material selected from the group consisting of polymethylmethacrylate (PMMA), polycarbonate (PC), polynorbornene, COC (Cyclic Olefin Copolymer), fluorinated polyimide, polystyrene (PS), SBC (Styrene Butadiene Copolymer), ABS (Acrylonitrile Butadiene Styrene), SAN (Styrene AcryloNitrile), and polysulfone. A common plastic substrate is more inexpensive relative to a common glass substrate and does not require a separate surface treatment. Furthermore, the plastic substrate is flexible unlike a fragile glass substrate, and thus is excellent in transport, storage, and handling. In addition, a transparent plastic substrate enables easy signal detection due to no fluorescence emission.

In the present invention, the epoxy group-containing polymer may be any polymer having an epoxy group but is preferably a copolymer of an epoxy group-containing acrylate monomer and an epoxy group-free acrylate monomer. The copolymer may be optionally selected according to the type of the plastic substrate. In particular, the content of epoxy groups in the copolymer can be adjusted by adjusting the weight ratio of the epoxy group-containing acrylate monomer. Furthermore, the use of an appropriate monomer can enhance proximity of the copolymer to PNAs.

In an embodiment of the present invention, the epoxy group-containing polymer is a copolymer of an epoxy group-containing acrylate monomer and a highly viscous acrylate monomer, as represented by formula 1 below:

<Formula 1> wherein $R^1$ is an epoxy group-containing ester, $R^3$ is hydrogen or an alkyl group, and X is a highly viscous acrylate compound.

In the present invention, the highly viscous acrylate monomer may be any acrylate monomer that can enhance UV-curable coating of acrylate (see T. Jaworek, *Macromol Symp.*, 159, 197, 2000; Cliff Roffey, "Photogeneration of Reactive Species for UV Curing", 1997). Preferably, the highly viscous acrylate monomer is an acrylate monomer with viscosity of 8-6,000 cp at 25° C., and is more preferably selected from the group consisting of dipentaerythritol hydroxypentaacrylate (DPHA), 9-ethyleneglycol diacrylate (9-EGDA), pentaerythritol tri-tetraacrylate (PETA), polyethyleneglycol 400 diacrylate, tripropyleneglycol diacrylate, trimethylol propane triacrylate, and dipentaerythritol hexaacrylate.

In another embodiment of the present invention, the epoxy group-containing polymer is a copolymer of an epoxy group-containing acrylate monomer and an adhesive acrylate derivative capable of being adhered to the plastic substrate, as represented by formula 2 below:

<Formula 2> wherein $R^1$ is an epoxy group-containing ester, $R^2$ is alkylester, and $R^3$ is hydrogen or an alkyl group.

In the present invention, the adhesive acrylate derivative may be any acrylate derivative which is similar to the type of a monomer constituting the plastic substrate so that a polymer composed of the acrylate derivative has similar physical properties to the plastic substrate to ensure easy adhesion of the polymer to the plastic substrate. Preferably, the adhesive acrylate derivative is selected from the group consisting of methylmethacrylate (MMA), ethylacrylate, ethylmethacrylate (EMA), n-propylacrylate, n-propylmethacrylate, isopropylacrylate, and isoproylmethacrylate. When the plastic substrate is made of polymethylmethacrylate (PMMA), it is particularly preferable to use methylmethacrylate (MMA) as the adhesive acrylate derivative since physical properties of PMMA are almost the same as those of MMA.

In the present invention, the content of epoxy groups in the epoxy group-containing polymer, i.e., the content of an epoxy group-containing acrylate monomer in the epoxy group-containing polymer may range from 0.1 to 100 wt %, preferably 10 wt % or more, and more preferably 20-30 wt %. If the content of epoxy groups is less than 10 wt %, it may be difficult to accumulate PNAs in narrow areas due to low epoxy group density, thereby decreasing a fluorescence signal. On the other hand, the epoxy group content above 40 wt % is not preferable since a PNA immobilization rate is not directly proportional to the density of epoxy groups. This might because relatively increased epoxy groups contained in a coating solution facilitate burial of surface epoxy groups, thereby preventing effective reaction of the surface epoxy groups with PNAs.

In the present invention, an amine terminal group of the probe PNA may directly bind with an epoxy group of the epoxy group-containing polymer coated on the plastic substrate. However, it is preferable to add a $C_{5-8}$ carboxylic acid linker having an amine group and presence or absence of ether to the amine terminal group of the probe PNA. The linker increases spatial directionality of the probe PNA, thereby optimizing PNA/DNA hybridization.

According to another aspect of the present invention, there is provided a method of manufacturing a PNA chip, the method including: mixing an epoxy group-containing acrylate monomer, a highly viscous acrylate monomer, and a photoinitiator in a ratio of 10-90:80-5:1-10; coating the mixture on a plastic substrate; curing the mixture by UV; and spotting a probe PNA printing solution on the plastic substrate.

According to still another aspect of the present invention, there is provided a method of manufacturing a PNA chip, the method including: mixing an epoxy group-containing acrylate monomer, an acrylate derivative having a similar physical property to a plastic substrate, and a radical initiator in a ratio of 10-99:1-89:0.1-0.5; radical-polymerizing the mixture; coating a solution obtained by dissolving the resultant polymer in a solvent on the plastic substrate; and spotting a probe PNA printing solution on the plastic substrate.

In the present invention, a base of an appropriate concentration, preferably 0.01-1.0 M, particularly preferably 0.05-0.5 M may be added to the probe PNA printing solution to efficiently perform a nucleophilic substitution reaction between an amine group of probe PNA and an epoxy group of a polymer to thereby assist immobilization of the probe PNA. The base may be a common base such as sodium hydroxide, potassium hydroxide, sodium carbonate, potassium carbonate, or Lewis acid.

The method of manufacturing the PNA chip in the presence of the radical initiator according to the present invention may further include storing the polymer-coated plastic substrate in a 30% or more humidity condition for 4 hours or more prior to spotting the probe PNA printing solution. If the polymer-coated plastic substrate is stored in a less than 30% humidity condition, a reaction efficiency between the epoxy group and the amine group may be lowered, thereby leading to signal reduction. It is preferable to store the polymer-coated plastic substrate in a 50-95% humidity condition. The polymer-coated plastic substrate is stored for 4 hours or more to evaporate an organic solvent.

According to yet another aspect of the present invention, there is provide a method of detecting SNP, the method including: applying a target DNA-containing reaction sample to the above-described PNA chip; hybridizing probe PNA with target DNA; washing the PNA chip to remove a nonspecific reaction product; and detecting a fluorescence signal based on PNA/DNA hybridization.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
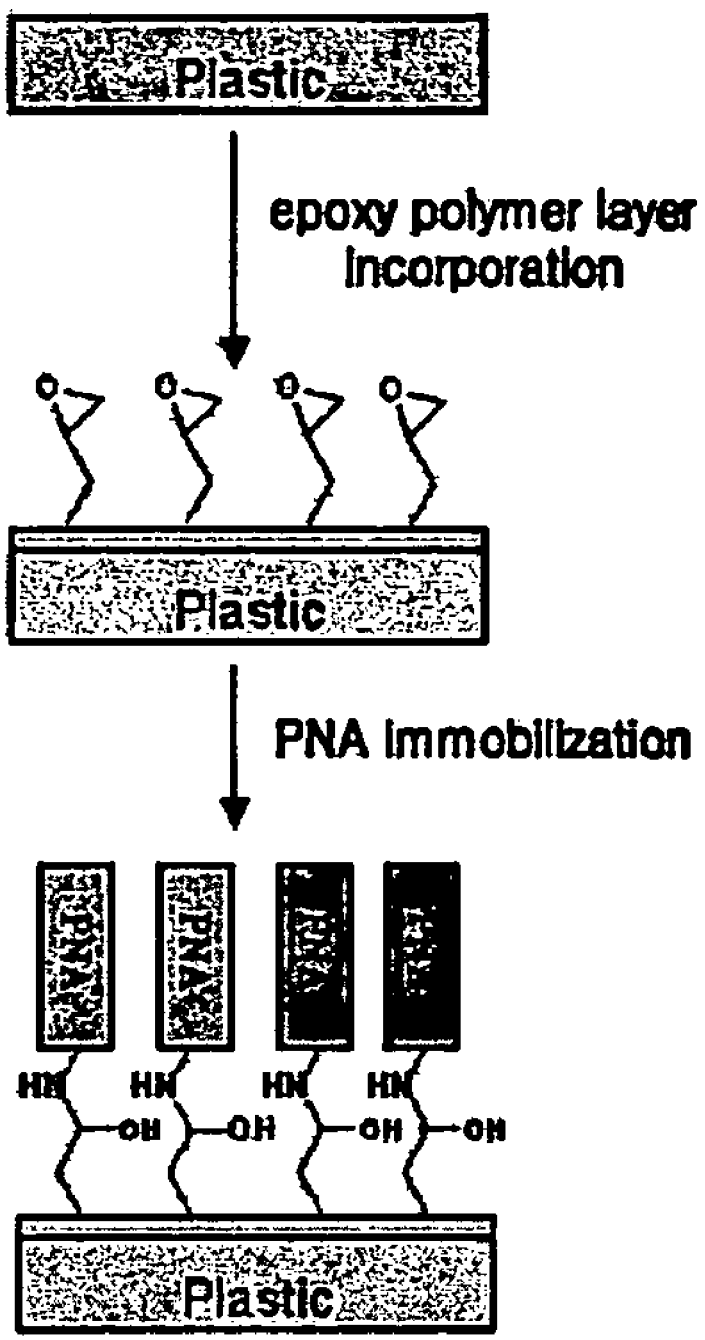
FIG. 1 is a schematic sequential diagram illustrating coating of an epoxy group-containing polymer layer on a universal plastic substrate and immobilization of PNAs onto the polymer layer according to the present invention.

The present invention will now be described more fully with reference to the accompanying drawings, in which exemplary embodiments of the invention are shown.

The present invention provides an epoxy group-containing polymer material for biomolecule immobilization, as represented by formula 1 or 2 below:

$$—[CR^3R^3—CR^1R^3—X]_n—$$  <Formula 1>

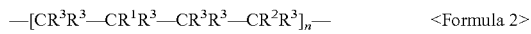
$$—[CR^3R^3—CR^1R^3—CR^3R^3—CR^2R^3]_n—$$  <Formula 2> wherein $R^1$ is an epoxy group-containing ester of $C_{3-12}$, $R^2$ is alkylester of $C_{2-16}$, $R^3$ is hydrogen or an alkyl group of $C_{1-16}$, X is a highly viscous acrylate compound, and n depends on a monomer concentration and a reaction duration but may be 10 to 2,000.

The polymer material is synthesized by UV curing (see T. Jaworek, *Macromol Symp.*, 159, 197, 2000; Cliff Roffey, 'Photogeneration of Reactive Species for UV Curing', 1997) or radical polymerization (see Bevington, J. C., in '*Comprehensive Polymer Science*', Vol 3, 65 1989; Tedder, J. M., *Angew. Chem., Int. Ed. Engl.*, 21, 401, 1982) using an acrylate compound.

In synthesis of the polymer material, two or more acrylate monomers may be used. Various combinations of the two or more acrylate monomers enable appropriate adjustment of the content of epoxy groups, thereby providing a polymer material with an appropriate epoxy group content.

In the case of forming a polymer coating layer by UV curing, an epoxy group-containing acrylate monomer and at least one highly viscous acrylate monomer are used. The acrylate monomers may be monomers having two or more vinyl groups. The present invention provides the composition of a UV curable coating solution, the composition ratio of the acrylate monomers, and efficient coating methods for UV curing.

In the case of forming a polymer coating layer by radical polymerization, an epoxy group-containing acrylate monomer, an acrylate derivative having a similar physical property to a plastic substrate, and a common radical initiator (azo-compound, peroxide, redox initiator) are used (Graeme moad, '*the chemistry of free radical polymerization*', 1995). As described above, the content of epoxy groups can be determined by the weight ratio of the epoxy group-containing acrylate monomer.

In the case of forming a polymer coating layer by thermal polymerization, in addition to an epoxy group-containing acrylate monomer, an alkylester-containing acrylate monomer is used.

In the formation of the polymer coating layer by UV curing, the highly viscous acrylate monomer may be dipentaerythritol hydroxypentaacrylate (DPHA), 9-ethyleneglycol diacrylate (9-EGDA), pentaerythritol tri-tetraacrylate (PETA), polyethyleneglycol 400 diacrylate, tripropyleneglycol diacrylate, trimethylol propane triacrylate, or dipentaerythritol hexaacrylate.

That is, the polymer coating layer formed by UV curing is composed of the epoxy group-containing acrylate monomer and at least one of the above-illustrated highly viscous acrylate monomers.

In the formation of the polymer coating layer by UV curing, the weight ratio of the epoxy group-containing acrylate monomer and the highly viscous acrylate monomer may range from 0.1:99.9 to 100:0. It is preferable to adjust the content of the epoxy group-containing acrylate monomer for biomolecule immobilization to 10 wt % or more.

The radical polymerization may be performed at 90° C. or less to prevent a ring-opening reaction of epoxy groups.

In the radical polymerization, the average molecular weight of a synthesized polymer can be adjusted by adjusting the reaction duration. It is preferable to perform the radical polymerization for 1 to 6 hours to prepare a desired coating solution and ensure coating transparency or crack prevention.

The radical polymerization is terminated by precipitation using excess alcohol such as methyl alcohol.

A polymer dried after the radical polymerization may be dissolved in tetrahydrofuran, dichloromethane, etc. to prepare a 0.1-5% polymer-containing coating solution. To prevent crack formation or provide transparency, it is preferable to prepare a 1-3% polymer-containing coating solution.

A substrate to be coated with the above-described polymer layer may be a common silicon wafer or glass, preferably a plastic substrate, and more preferably a transparent plastic substrate. Conventionally, a well-processed expensive glass is mainly used as a chip substrate. However, in the present invention, a common inexpensive plastic substrate with easy handling property is used to overcome the disadvantages of a glass substrate. Generally, the term "transparent plastic substrate" embraces substrates made of polymethylmethacrylate (PMMA), polycarbonate (PC), polynorbornene, COC (Cyclic Olefin Copolymer), fluorinated polyimide, polystyrene (PS), SBC (Styrene Butadiene Copolymer), ABS (Acrylonitrile Butadiene Styrene), SAN (Styrene AcryloNitrile) or polysulfone.

A coating of polymers for coating layer formation on plastic substrate may be accomplished by dipping, spraying, printing method etc. It is preferable that the polymer-coated plastic substrate is used after stored in a 50% or more humidity condition. If the polymer-coated plastic substrate is stored in a low humidity condition, PNA immobilization efficiency may be lowered.

According to the present invention, strong immobilization of biomolecules, i.e., PNAs on an epoxy group-containing plastic substrate can be accomplished by an easy and inexpensive method such as microarray spotting in the presence of an appropriate concentration of a base (sodium hydroxide, potassium hydroxide, sodium carbonate, potassium carbonate, Lewis acid).

According to the present invention, a printing buffer containing a basic catalyst is prepared to bind amine groups of PNAs to epoxy groups coated on a substrate. Injection of the printing buffer using an inkjet arrayer provides easy and inexpensive immobilization of PNAs on a substrate surface. Preferably, the immobilization of PNAs is performed at about 23° C. in a 50-60% humidity condition.

The present invention provides optimal buffer solutions, reaction conditions, and efficient washing methods necessary for specific PNA/DNA hybridization using the above-prepared PNA array.

A buffer solution for PNA/DNA hybridization may be a buffer solution containing 5×SSC, 50 mM HEPES, 1% SDS, and 0.1% BSA. There is no need to perform a separate blocking process to prevent nonspecific hybridization.

After the PNA/DNA hybridization, there may be used four washing buffer solutions containing 1×, 0.1×, 0.01×, and 0.001×SSC (5 minutes for each), respectively.

Hereinafter, the present invention will be described more specifically with reference to the following examples. The following examples are for illustrative purposes and are not intended to limit the scope of the invention.

Example 1

Preparation of Epoxy Group-Containing Polymer-Coated Substrate by UV Curing

Glycidoxymethylmethacrylate (GMA) intended for epoxy group incorporation, 9-ethyleneglycol diacrylate (9-EGDA), and a photoinitiator (Irgacure 184, Ciba-Geigy Chemical Co.) were mixed in an appropriate ratio (10-90:80-5:1-10). After the photoinitiator was completely dissolved, the resultant mixture was coated on a polymethylmethacrylate (PMMA) substrate using a spin coater at 500 rpm for 6 seconds and then at 1,000-4,000 rpm for 20 seconds. Then, the resultant substrate was exposed to 254 nm UV in a nitrogen environment and dried. The above method is not limited to an acrylate monomer and a plastic substrate and may be applied to various types of monomers and substrates. The thus produced epoxy group-containing polymer had the following formula: $-[CH_2C(CH_3)(C(O)OCH_2CHCH_2)CH_2CH(C(O)O(CH_2CH_2O)_9C(O)CHCH_2)]n-$. The UV curing using DPHA or PETA instead of 9-EGDA can produce a polymer of GMA and DPHA or PETA. FIG. 1 is a schematic sequential diagram illustrating coating of an epoxy group-containing polymer layer on a universal plastic substrate and immobilization of PNAs onto the epoxy group-containing polymer layer according to the present invention.

Example 2

Preparation of Epoxy Group-Containing Polymer-Coated Substrate by Radical Polymerization Glycidoxymethylmethacrylate (GMA) intended for epoxy group incorporation, methylmethacrylate (MMA), a radical initiator (2,2,6,6-tetramethyl-4-piperidinol, TMPO), and a molecular weight adjustor were mixed in an appropriate ratio (99-10:1-89:0.1-0.5:0.1-0.5). The mixture was made heated at 75° C. for 2 hours and then at 90° C. for 0.5-3 hours. Considering that the viscosity of the reaction mixture was greatly changed according to the weight ratio of MMA, the reaction was terminated before the reaction mixture was completely solidified. When the viscosity of the reaction mixture reached an appropriate level, excess methyl alcohol was added to it, which is vigorously stirred, and recrystallized. The resultant crystals were dried in vacuum for one day. The thus obtained polymer was evaluated for the content of epoxy groups by NMR and for average molecular weight by GPC. 0.1-5 wt % of the polymer was dissolved in tetrahydrofuran. A PMMA substrate was fixed on a spin coater and coated 2 ml of the polymer-containing coating solution by spin-coater (see FIG. 1). The epoxy group-containing polymer had the following formula: $-[CH_2C(CH_3)(C(O)OCH_2CHCH_2)CH_2C(CH_3)(C(O)OCH_3)]n-$, and an average molecular weight (Mw) of 75,000 to 250,000. A polymer of GMA and EMA can be prepared in the same manner as in the above-described radical polymerization using EMA instead of MMA.

Figure 4:
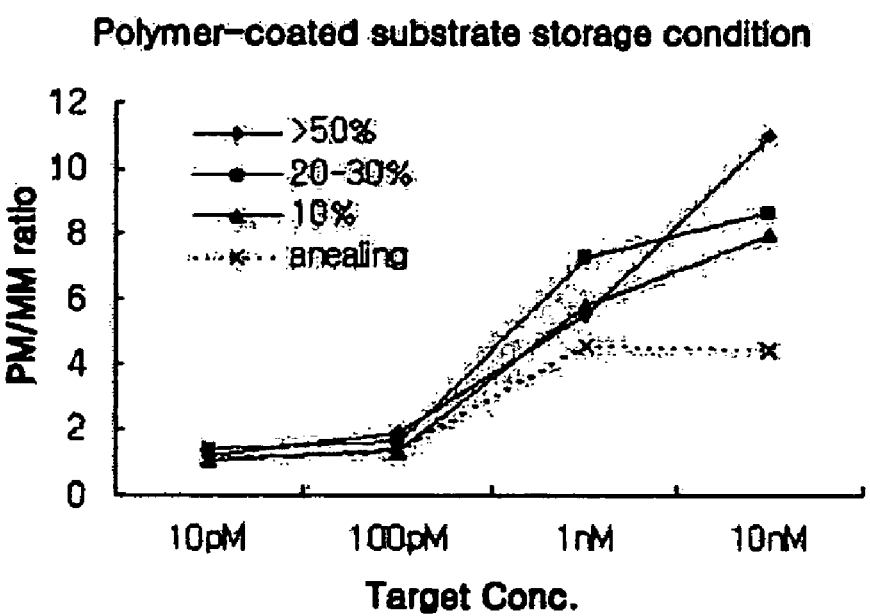
FIG. 4 illustrates PNA/DNA hybridization results for PNA arrays to determine the optimal storage condition of the polymer-coated plastic substrate prior to PNA immobilization.

The polymer-coated substrate was stored in a 50% or more humidity condition for 4 hours or more before use. If the polymer-coated substrate is stored in a low humidity condition, reaction efficiency between epoxy groups and amine groups may be lowered, resulting in signal reduction. FIG. 4 illustrates PNA/DNA hybridization results for PNA arrays to determine the optimal storage condition of the polymer-coated plastic substrate prior to PNA immobilization. The plastic substrate coated the epoxy group-containing polymer was exposed to various humidity conditions (10, 20-30, >50%). In FIG. 4, PM/MM ratio represents the average fluorescence signal ratio of a perfect match (PM) to a mismatch (MM) in DNA/PNA hybridization, and a signal difference between PM and MM results from a single base difference. A higher PM/MM ratio represents more excellent specificity of probe PNAs to target DNAs. Referring to FIG. 4, when the polymer-coated substrate was stored in 30% or more, preferably 50% or more humidity conditions, signal sensitivity (PM/MM ratio) was more excellent.

Example 3

PNA-Cy3 Immobilization

Figure 2A:
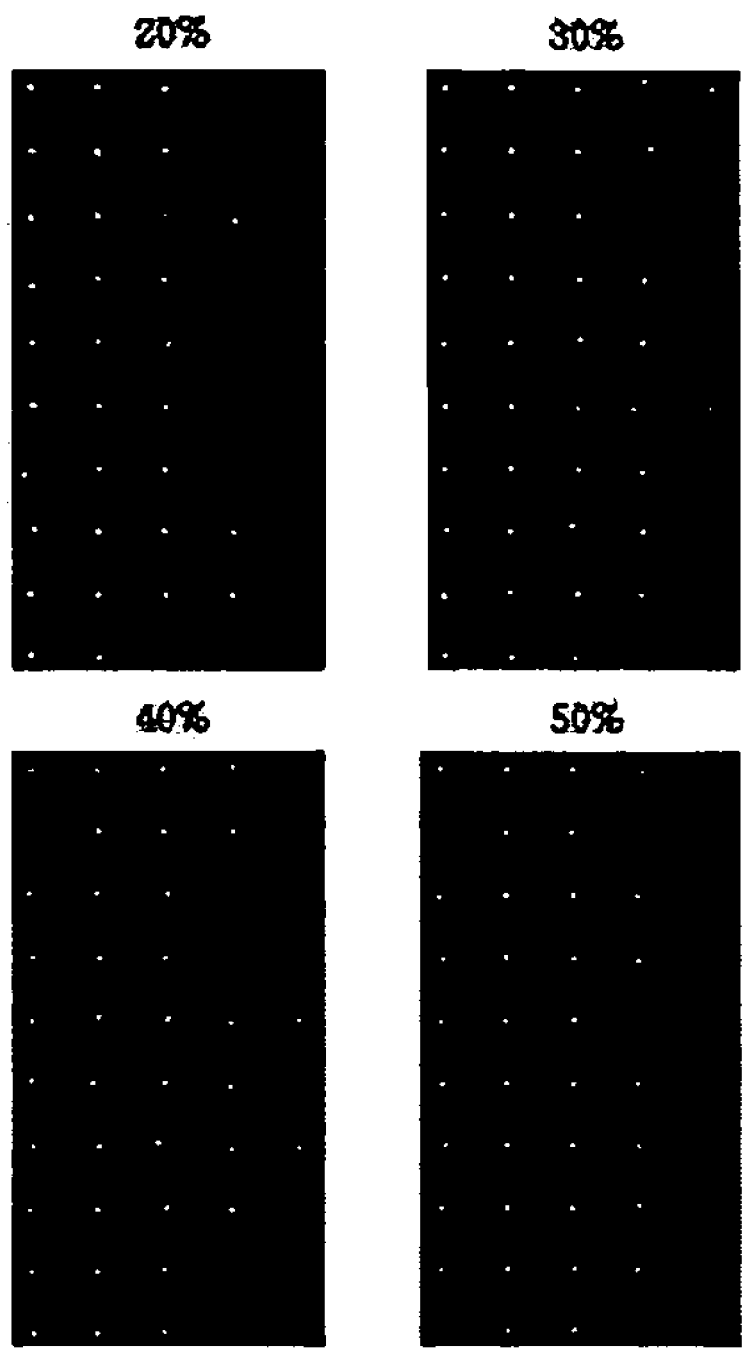
FIGS. 2A and 2B are respectively fluorescence images and array information for evaluation results of a PNA immobilization rate with respect to the content of epoxy groups in a polymer layer according to the present invention.
Figure 2B:
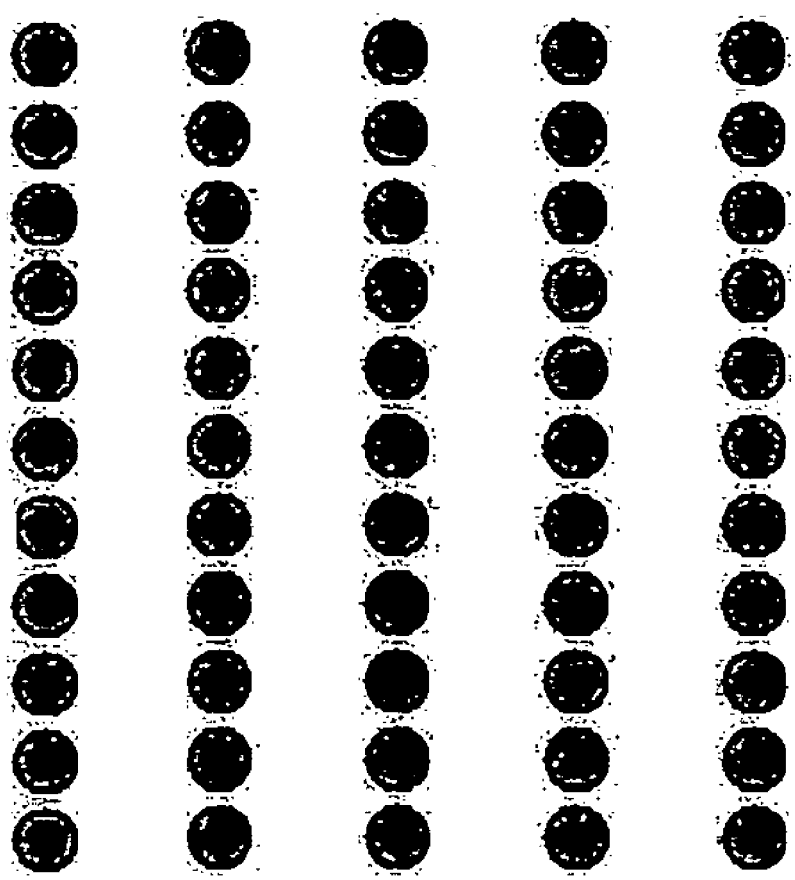
Figure 3:
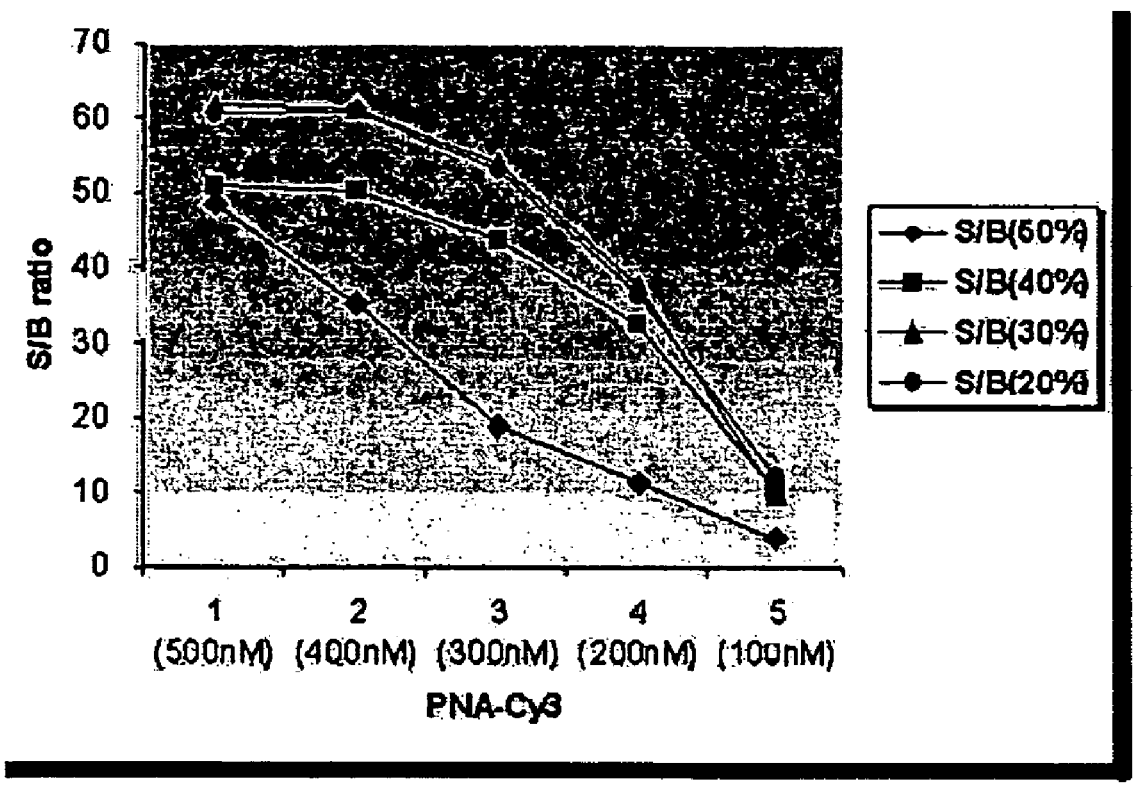
FIG. 3 is graphic quantitative analysis data for the fluorescence images of FIG. 2A.

In this Example, degree of PNA immobilization with respect to GMA content was evaluated using the polymer-coated plastic substrates prepared in Examples 1 and 2. For this, Cy3-labelled PNA rtL-180w (PNAGENE. Inc) is immobilized on the above substrate. Printing solution preparation and spotting were performed according to the following Example 4. The plastic substrates had different epoxy contents of 20%, 30%, 40%, and 50% by adjusting the GMA content. The degree of immobilization of the PNA rtL-180W could be directly determined by fluorescence intensity of the Cy3-labelled PNA rtL-180w. In this experiment, the different concentration of PNAs were tried, i.e., 500, 400, 300, 200, and 100 nM. Fluorescence images and array information for PNAs immobilized on the substrate containing the different contents of epoxy groups are respectively illustrated in FIGS. 2A and 2B. FIG. 3 is graphic quantitative analysis data for the fluorescence images of FIG. 2A. In FIG. 3, the fluorescence intensity (S/B ratio) of a spotting composition containing no PNA-cy3 was used as a background signal. Referring to FIG. 3, PNA immobilization rate was the greatest at the epoxy contents of 20% and 30%. Even at the epoxy contents of 40% and 50%, PNA immobilization occurred with no problem. The PNA rtL-180w used in this Example had the following sequence:

```
rtL180w:
                                        (SEQ ID NO: 2)
N terminal (5') - GTTTCTCC*TGGCT- C terminal (3')-Cy3
```

Example 4

Printing Solution Preparation and PNA Array Fabrication

PNA oligonucleotides (13-mer, PANAGENE, Inc.) were dissolved in 50 uM distilled water. As the PNA oligonucleotides, there were used PNA A, rtL-180w, and rtL-180m. The PNA A was used as a positive control of PNA/DNA hybridization. The rtL-180w was a specific sequence of HBV (hepatitis B virus) RNA polymerase (Geneln, Inc.), and the rtL-180m was a changed sequence of HBV RNA polymerase resulting in lamivudine-resistance. The difference between the rtL-180w and the rtL-180m was only one base (C-A). The rtL-180w and the rtL-180m were used as test sequences for identification of SNPs (Single Nucleotide Polymorphisms). A 0.1N NaOH solution was used to assist PNA immobilization. For each of the PNA A, the rtL-180w, and the rtL-180m, the solution obtained by dissolving the PNA oligonucleotides in the distilled water and the NaOH solution were mixed in a ratio of 1:1-0.5 and loaded in a 96-well plate. The prepared samples were spotted on PMMA substrates using an inkjet arrayer (Cartesian) and then stored in humidity of 50% or more and at a temperature of 23-24° C. for 16 hours to induce sufficient reaction between epoxy groups and amine groups. During the spotting, humidity was increased to uniformly maintain a spot size.

The probe PNA oligonucleotides (13-mers) used in this Example had the following sequences:

```
Probe A (artificial sequence):
                                          (SEQ ID NO: 1)
N terminal (5') - TTCCACCAGATGG - C terminal (3')

Probe W (rtL-180w):
                                          (SEQ ID NO: 2)
N terminal (5') - GTTTCTCC*TGGCT- C terminal (3')

Probe M (rtL-180m):
                                          (SEQ ID NO: 3)
N terminal (5') - GTTTCTCA*TGGCT- C terminal (3')
```

Example 5

On-Chin-Reaction and SNP Detection

Figure 5A:
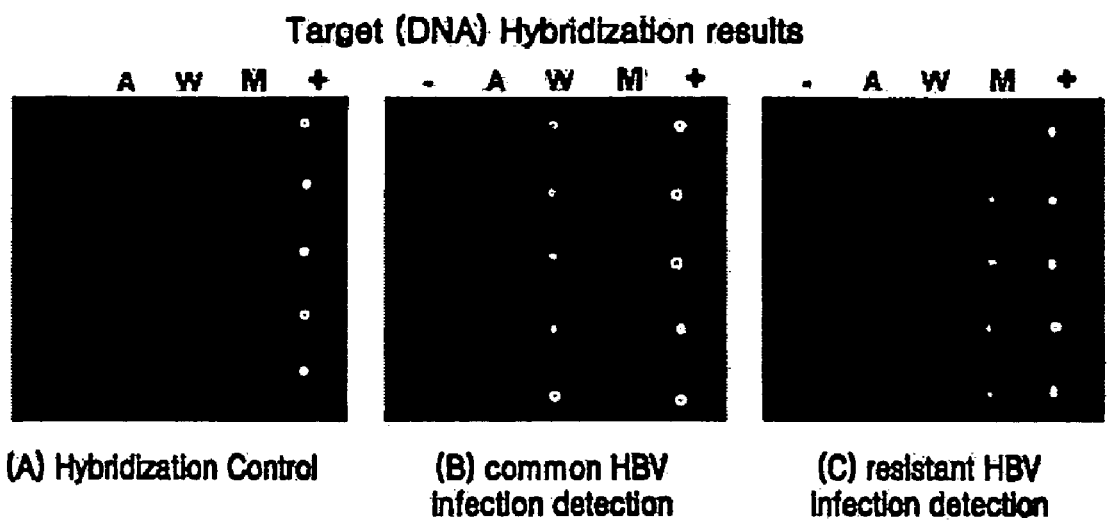
FIGS. 5A and 5B are respectively fluorescence image analysis data for PNA/DNA hybridization results with respect to target DNAs and array information.
Figure 5B:
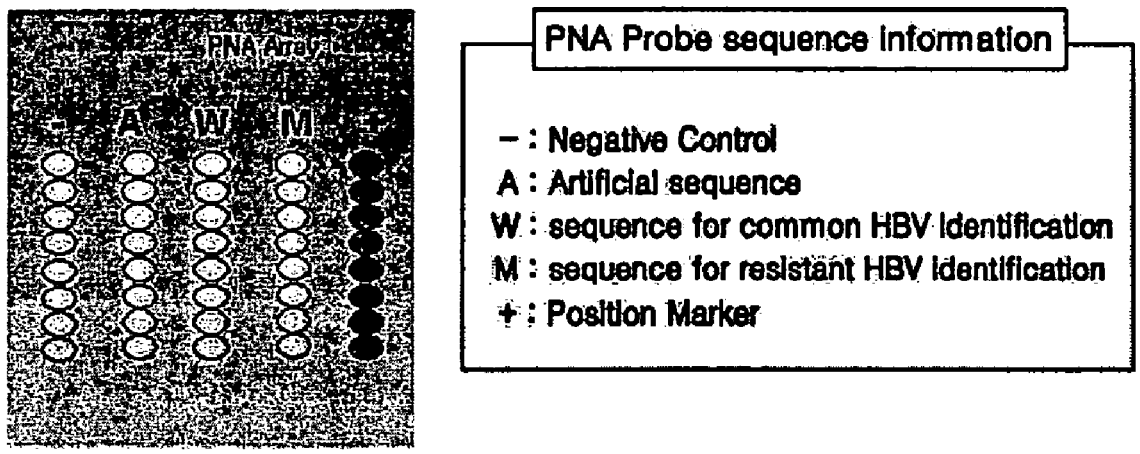
Figure 6A:
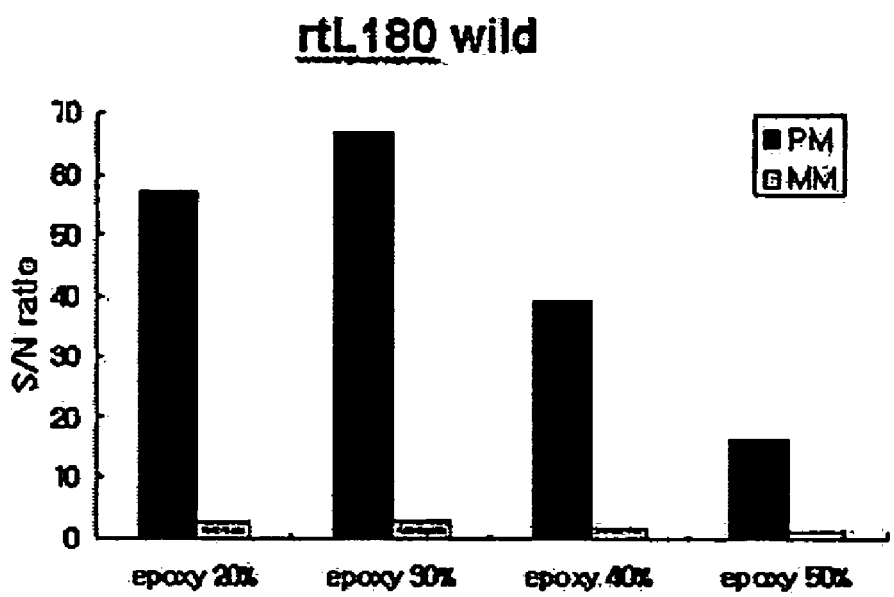
FIGS. 6A and 6B are graphic quantitative analysis data for PNA/DNA hybridization results with respect to the content of epoxy groups for rtL 180 wild and rtL 180 mutant, respectively.
Figure 6B:
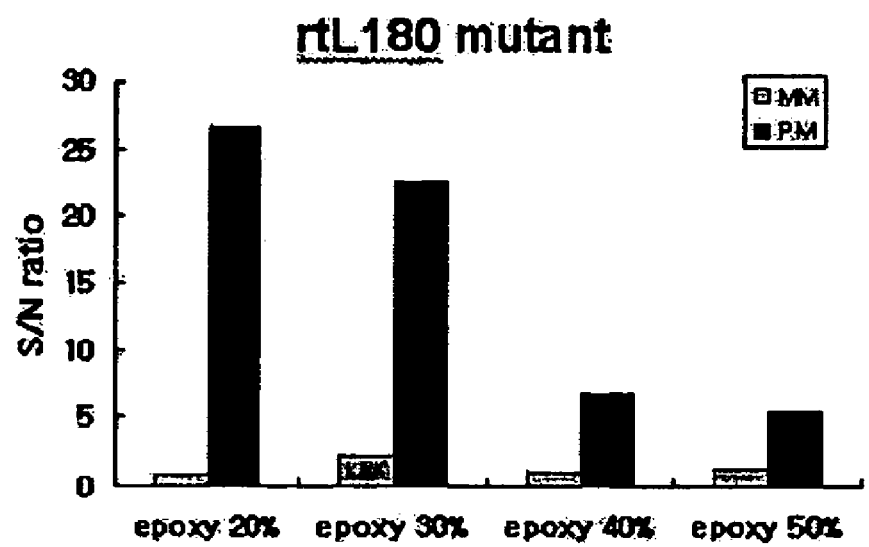

The PNA-immobilized PMMA substrates prepared in Example 4 were washed with distilled water for 5 minutes to remove residual NaOH followed by hybridization without separate blocking. There was used a hybridization buffer containing 5×SSC (pH 7.0 buffer containing sodium chloride and sodium citrate), 50 mM HEPES, 1% SDS, and 0.1% BSA. DNAs (1 pM~100 nM) labeled with fluorescent dye, named cyanine3 (Cy3) were used as targets. A target DNA in hybridization solution was denatured at 94° C. for 5 minutes and then incubated at 42° C. for 60 minutes. Generally, PNAs have a one degree higher melting temperature (Tm) (per one base) relative to DNAs. To remove nonspecific PNA/DNA hybridization, washing was performed using a 1×SSC buffer, a 0.1×SSC buffer, a 0.01×SSC buffer, and a 0.001×SSC buffer (5 minutes for each). Then, PNA arrays were subjected to complete moisture removal, and fluorescence signals resulted from DNA/PNA hybridization were measured using a fluorescence detection laser scanner (Axon Instrument, Inc.) under conditions of focus position 65 and PMT 400. Fluorescent images for the PNA/DNA hybridization results using different target DNAs and array information are respectively illustrated in FIGS. 5A and 5B. Complementary DNA oligonucleotides to the artificial PNA sequence (positive control), for identifying common HBV infection, and for identifying lamivudine-resistant HBV infection were respectively used as target DNAs in (A), (B), and (C) of FIG. 5A. Referring to FIGS. 5A and 5B, the probe PNAs were specifically hybridized with the corresponding target DNAs. FIGS. 6A and 6B illustrate graphic quantitative analysis data for PNA/DNA hybridization results with respect to the content of epoxy groups for the rtL-180w and rtL-180m, respectively. From FIGS. 6A and 6B, it can be seen that PNA/DNA hybridization occurs at the greatest level at epoxy contents of 20% and 30%.

The target DNA oligonucleotides (13-mers) used in this Example had the following sequences:

```
Target A: 5' Cy3- CCATCTGGTGGAA-3'    (SEQ ID NO: 4)

Target W: 5' Cy3- AGCCAG*GAGAAA-3'    (SEQ ID NO: 5)

Target M: 5' Cy3- AGCCAT*GAGAAA-3'.   (SEQ ID NO: 6)
```

Example 6

PNA/DNA Hybridization by PNA Linker

Figure 7A:
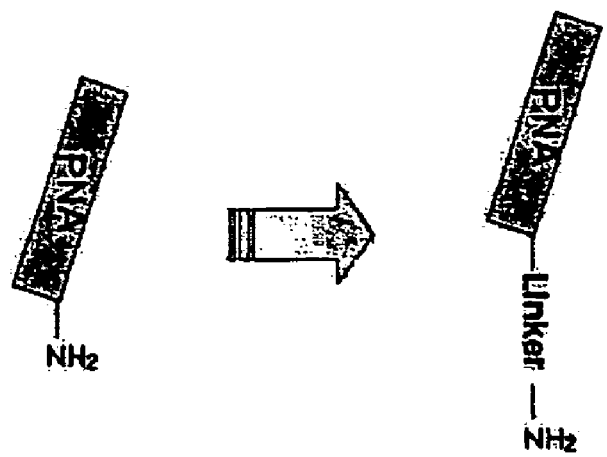
FIG. 7A is a schematic diagram illustrating a linker used for optimizing PNA/DNA hybridization according to the present invention and FIG. 7B illustrates chemical structural formulae for various types of the linker.
Figure 7B:
Figure 7B:
Figure 7B:
Figure 8A:
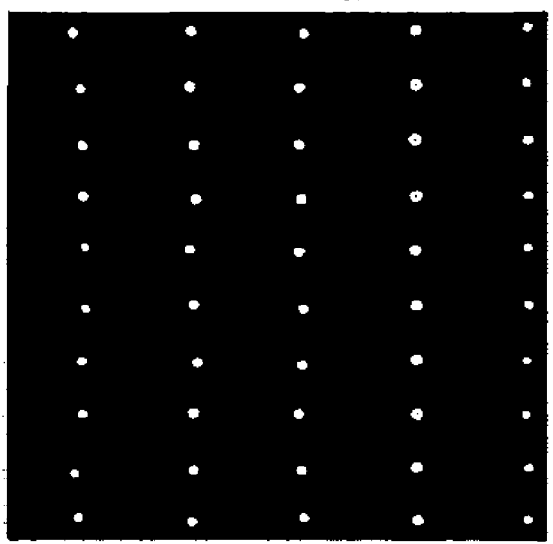
FIGS. 8A and 8B are respectively fluorescence images and spot arrays for PNA/DNA hybridization mediated by linkers according to the present invention.
Figure 8A:
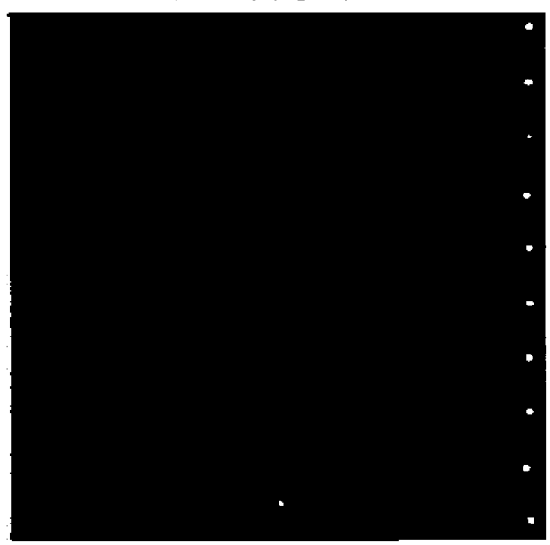
Figure 8A:
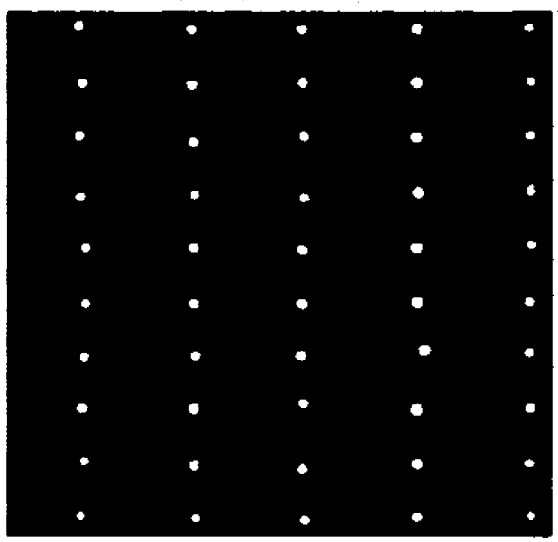
Figure 8A:
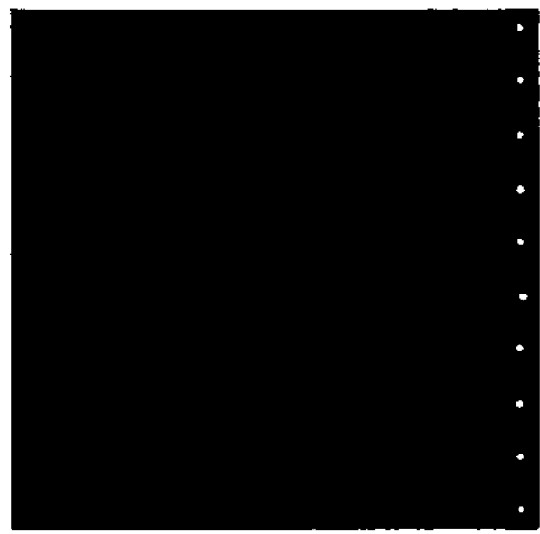
Figure 8B:
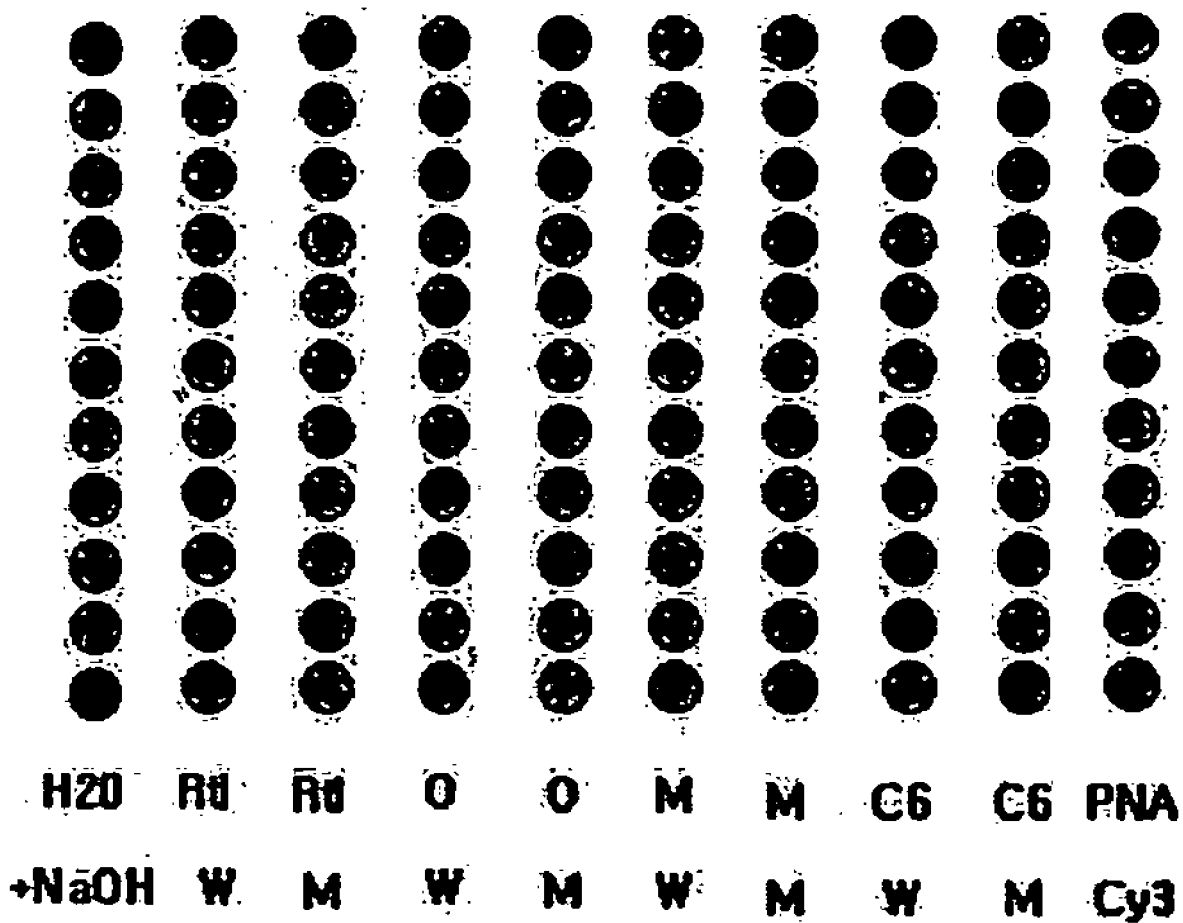
Figure 9A:
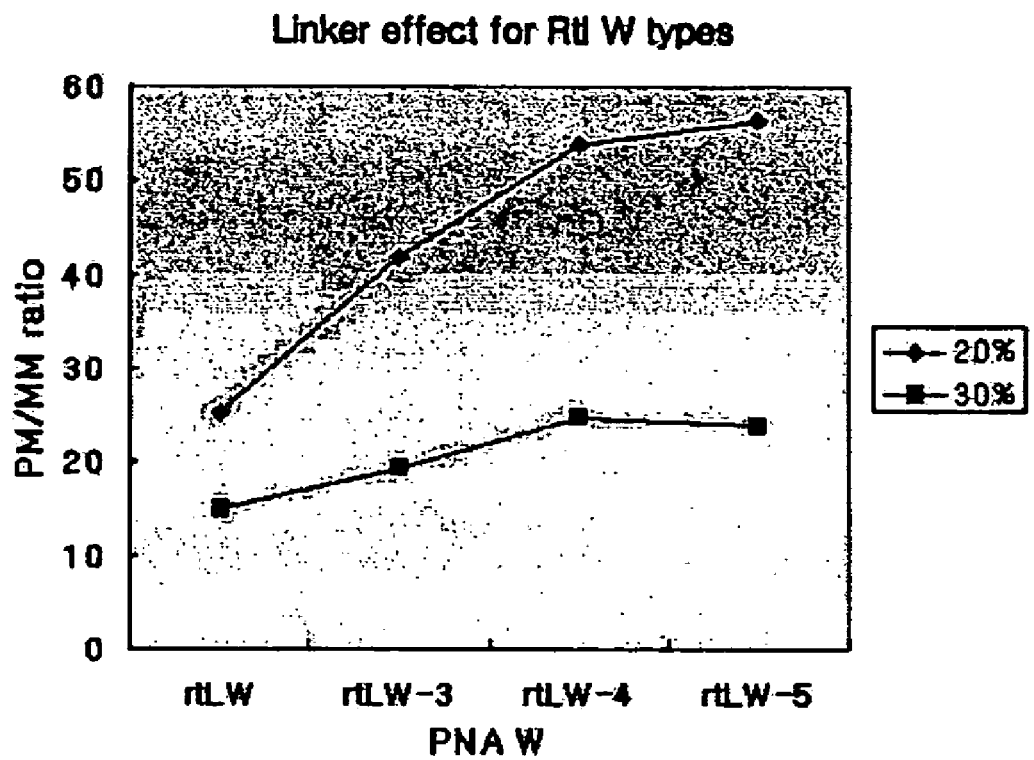
FIGS. 9A and 9B are graphic quantitative analysis data for the fluorescence images of FIG. 8A.
Figure 9B:
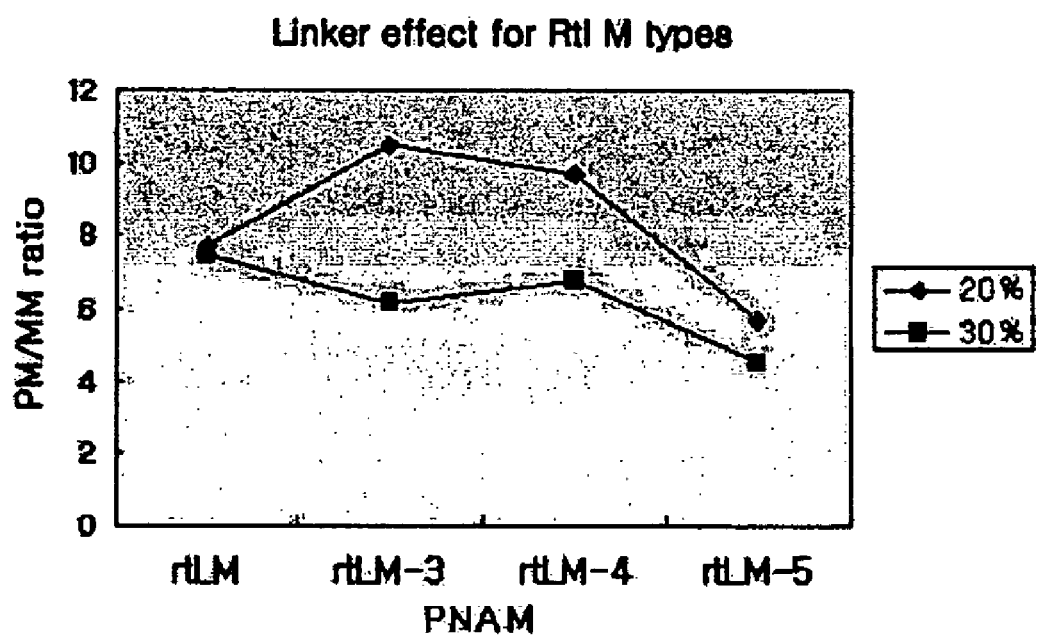

To optimize PNA/DNA hybridization, a $C_{5-8}$ amine group-containing acid which functions as a spacer was attached to the amine terminal groups of PNAs. FIG. 7A is a schematic diagram illustrating a linker used for optimizing PNA/DNA hybridization according to the present invention and FIG. 7B illustrates chemical structural formulae for various types of the linker. In FIG. 7B, a O-linker is 2-(2-aminoethoxy)ethoxy acetic acid, an M-linker is 2-aminoethoxy acetic acid, and a C-linker is 6-aminohexanoic acid. The amine group-containing acid is attached to PNAs via a peptide bond, and an amine group of the amine group-containing acid reacts with an epoxy group of an epoxy-group containing polymer layer like in the above-described Examples to immobilize the PNAs onto the polymer layer. The linkers attached to PNA prevent the immobilized PNA from aggregation on the surface and make PNA molecules representative to the target DNA molecules. As a result, the linker which functions as a spacer improve accessibility of probe PNA to the target DNA. In this Example, there were used epoxy group-containing polymer-coated substrates with epoxy contents of 20% and 30% providing the greatest efficiency of PNA immobilization and PNA/DNA hybridization. PNA immobilization and PNA/DNA hybridization were performed in the same manner as in Examples 4 and 5 except that a linker was used. Fluorescence images and array information for evaluation results of PNA/DNA hybridization mediated by various types of linkers are respectively illustrated in FIGS. 8A and 8B. The types of linkers and PNAs are represented in the spot arrays of FIG. 8B. In FIG. 8B, $H_2O$+NaOH is a negative control, rtL-W(M) is common wild-type (mutant) PNAs with no linkers, O-W (M) is O-linker attached rtLW(M) PNAs, M-W(M) is M-linker attached rtLW(M) PNAs, and C6-W is C6-linker attached rtLW PNAs. PNA-cy3 is used as a position marker. FIGS. 9A and 9B are graphic quantitative analysis data of the fluorescence images of FIG. 8A. In FIGS. 9A and 9B, rtLW (M) is linker-free common wild-type (mutant) PNAs, rtLW (M)-3 is O-linker attached rtLW(M) PNAs, rtLW(M)-4 is M-linker attached rtLW(M) PNAs, and rtLW(M)-5 is C6-linker attached rtLW(M) PNAs. From FIGS. 9A and 9B, it can be seen that linker-attached probe PNAs exhibit more excellent specificity to target DNAs relative to linker-free probe PNAs.

The sequences of the linker-attached probe PNAs used in this Example were as follows:

```
W(rtL180w)-linker:
5' Cy3- AGCCAG*GAGAAA-3'- Linker

M(rtL180m)-linker:
5' Cy3- AGCCAT*GAGAAA-3'- Linker
```

Example 7

Sensitivity Evaluation of PNA Arrays for PNA/DNA Hybridization

Figure 10A:
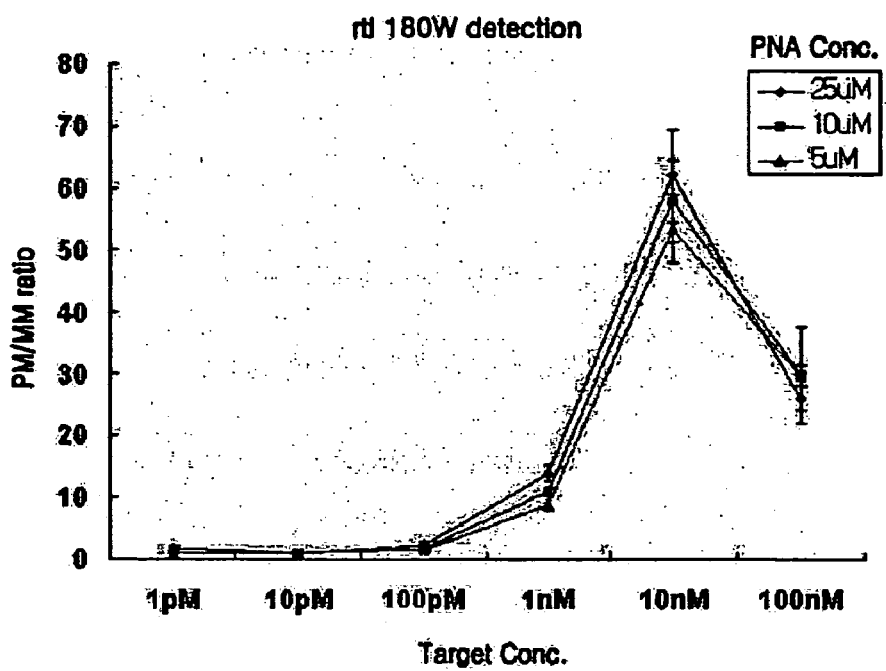
FIGS. 10A and 10B are quantitative analysis data for detection sensitivity of PNA/DNA hybridization with respect to the concentration of probe PNAs.
Figure 10B:
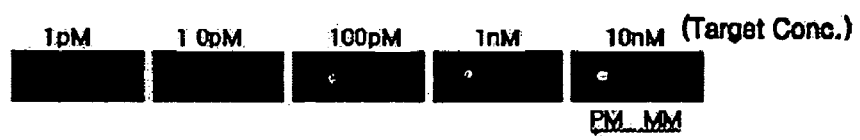

The polymer-coated substrates prepared in Examples 1 and 2 were spotted with 10 uM or 5 uM of PNA which were lower concentration than those of commonly known PNA. The sensitivity of target DNA in PNA/DNA hybridization was evaluated according to the methods described in Examples 4 and 5. Hybridization intensity of features spotted 5 uM PNA(low concentration) showed the similar level with those of 25 uM PNA. This might be because PNAs exhibit a higher binding affinity than DNAs due to a higher Tm value than DNAs, and no repulsive force due to no chargeability. FIGS. 10A and 10B illustrate quantitative analysis data for detection sensitivity of PNA/DNA hybridization with respect to the concentration of probe PNAs.

As described above, according to the present invention, probe PNAs can be immobilized on a universal plastic substrate in an efficient and cost-effective manner. The use of the probe PNA-immobilized substrate enables detection of various gene variations. Furthermore, it is anticipated that the use of PNA chips based on excellent physicochemical properties of PNAs can overcome the disadvantages of common DNA chips.

What is claimed is:

1. A PNA (Peptide Nucleic Acid) chip in which a probe PNA containing a desired DNA sequence is immobilized on a plastic substrate coated with an epoxy group-containing polymer, wherein the epoxy group-containing polymer is a copolymer of an epoxy group-containing acrylate monomer and an epoxy group-free acrylate monomer wherein the content of epoxy groups in the epoxy group-containing polymer ranges from 20 to 30 wt %.

2. The PNA chip of claim 1, wherein the plastic substrate is a transparent plastic substrate made of a material selected from the group consisting of polymethylmethacrylate (PMMA), polycarbonate (PC), polynorbornene, COC (Cyclic Olefin Copolymer), fluorinated polyimide, polystyrene (PS), SBC (Styrene Butadiene Copolymer), ABS (Acrylonitrile Butadiene Styrene), SAN (Styrene AcryloNitrile), and polysulfone.

3. The PNA chip of claim 1, wherein the epoxy group-containing polymer is a copolymer of an epoxy group-containing acrylate monomer and a highly viscous acrylate monomer, as represented by formula 1 below:

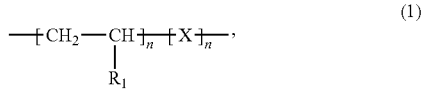

(1)

wherein $R^1$ is an epoxy group-containing ester, and X is a highly viscous acrylate compound.

4. The PNA chip of claim 3, wherein the highly viscous acrylate monomer is selected from the group consisting of dipentaerythritol hydroxypentaacrylate (DPHA), 9-ethyleneglycol diacrylate (9-EGDA), pentaerythritol tri-tetraacrylate (PETA), polyethyleneglycol 400 diacrylate, tripropyleneglycol diacrylate, trimethylol propane triacrylate, and dipentaerythritol hexaacrylate.

5. The PNA chip of claim 1, wherein the epoxy group-containing polymer is a copolymer of an epoxy group-containing acrylate monomer and an adhesive acrylate derivative capable of being adhered to the plastic substrate, as represented by formula 2 below:

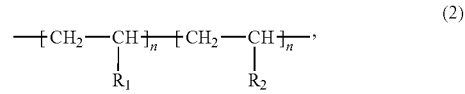

(2)

wherein $R^1$ is an epoxy group-containing ester and $R^2$ is alkylester.

6. The PNA chip of claim 5, wherein the adhesive acrylate derivative is selected from the group consisting of methylmethacrylate (MMA), ethylacrylate, ethylmethacrylate (EMA), n-propylacrylate, n-propylmethacrylate, isopropylacrylate, and isopropylmethacrylate.

7. The PNA chip of claim 1, wherein a $C_{5-8}$ carboxylic acid linker having an amine group and presence or absence of ether is attached to an amine terminal group of the probe PNA.

* * * * *

SEQUENCE LISTING

```
<160> NUMBER OF SEQ ID NOS: 6

<210> SEQ ID NO 1
<211> LENGTH: 13
<212> TYPE: DNA
<213> ORGANISM: Artificial
<220> FEATURE:
<223> OTHER INFORMATION: Synthetic construct

<400> SEQUENCE: 1
ttccaccaga tgg                                                      13

<210> SEQ ID NO 2
<211> LENGTH: 13
<212> TYPE: DNA
<213> ORGANISM: Artificial
<220> FEATURE:
<223> OTHER INFORMATION: Synthetic construct  rtL180w

<400> SEQUENCE: 2
gtttctcctg gct                                                      13

<210> SEQ ID NO 3
<211> LENGTH: 13
<212> TYPE: DNA
<213> ORGANISM: Artificial
<220> FEATURE:
<223> OTHER INFORMATION: Synthetic construct  rtL180m

<400> SEQUENCE: 3
gtttctcatg gct                                                      13

<210> SEQ ID NO 4
<211> LENGTH: 13
<212> TYPE: DNA
<213> ORGANISM: Artificial
<220> FEATURE:
<223> OTHER INFORMATION: Synthetic construct

<400> SEQUENCE: 4
ccatctggtg gaa                                                      13
```

-continued

```
<210> SEQ ID NO 5
<211> LENGTH: 12
<212> TYPE: DNA
<213> ORGANISM: Artificial
<220> FEATURE:
<223> OTHER INFORMATION: Synthetic construct  W Target sequence

<400> SEQUENCE: 5
agccaggaga aa                                                          12

<210> SEQ ID NO 6
<211> LENGTH: 12
<212> TYPE: DNA
<213> ORGANISM: Artificial
<220> FEATURE:
<223> OTHER INFORMATION: Synthetic construct  M Target sequence

<400> SEQUENCE: 6
agccatgaga aa                                                          12
```